US009574984B2

(12) United States Patent
Takeda et al.

(10) Patent No.: US 9,574,984 B2
(45) Date of Patent: Feb. 21, 2017

(54) PARTICLE BEAM FORMING DEVICE

(71) Applicants: FUJI ELECTRIC CO., LTD., Kawasaki-shi, Kanagawa (JP); THE UNIVERSITY OF TOKYO, Bunkyo-ku, Tokyo (JP)

(72) Inventors: Naoki Takeda, Yokohama (JP); Masaya Tabaru, Hino (JP); Kazuhiro Koizumi, Sagamihara (JP); Noritomo Hirayama, Hino (JP); Nobuyuki Takegawa, Tokyo (JP); Takuma Miyakawa, Tokyo (JP)

(73) Assignees: FUJI ELECTRIC CO., LTD, Kawasaki-Shi, Kanagawa (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/432,948

(22) PCT Filed: Oct. 17, 2013

(86) PCT No.: PCT/JP2013/078138
§ 371 (c)(1),
(2) Date: Apr. 1, 2015

(87) PCT Pub. No.: WO2014/087746
PCT Pub. Date: Jun. 12, 2014

(65) Prior Publication Data
US 2015/0260629 A1 Sep. 17, 2015

(30) Foreign Application Priority Data
Dec. 3, 2012 (JP) ................................ 2012-264287

(51) Int. Cl.
*G01N 21/00* (2006.01)
*G01N 15/02* (2006.01)
(Continued)

(52) U.S. Cl.
CPC ....... *G01N 15/0211* (2013.01); *G01N 15/0255* (2013.01); *G01N 21/4788* (2013.01); *H01J 49/04* (2013.01); *G01N 2015/0216* (2013.01)

(58) Field of Classification Search
CPC ........... G01N 15/0255; G01N 15/0211; G01N 21/3504; G01N 1/2208; H01J 49/0095; H01J 49/067; H01J 49/0445; B01D 45/06
(Continued)

(56) References Cited

U.S. PATENT DOCUMENTS 3,960,449 A * 6/1976 Carleton ........... G01N 15/1434 250/574
H755 H * 3/1990 Karl, Jr. ................ G01N 21/62 250/458.1
(Continued)

FOREIGN PATENT DOCUMENTS

JP 06201567 A 7/1994
JP 2002505423 A 2/2002
(Continued)

OTHER PUBLICATIONS

Japanese Office Action (and English translation thereof) dated Jun. 24, 2015, issued in counterpart Japanese Application No. 2014-519734.
(Continued)

*Primary Examiner* — Tarifur Chowdhury
*Assistant Examiner* — Isiaka Akanbi
(74) *Attorney, Agent, or Firm* — Holtz, Holtz & Volek PC

(57) ABSTRACT

A particle beam forming device for forming either a linear or conical particle beam from a particle source in which particles are dispersed in a gas, includes: a reduced-pressure vessel in which pressure is reduced; a particle beam generating unit, which has one end arranged outside of the
(Continued)

reduced-pressure vessel and an other end arranged inside the reduced-pressure vessel, and which captures the particle source from outside the reduced-pressure vessel and introduces the particle beam into the reduced-pressure vessel; and a particle beam evaluating unit for evaluating a spatial distribution of the particle beam inside the reduced-pressure vessel.

8 Claims, 16 Drawing Sheets

(51) Int. Cl.
*H01J 49/04* (2006.01)
*G01N 21/47* (2006.01)

(58) Field of Classification Search
USPC .................................... 356/338, 72; 250/288
See application file for complete search history.

(56) References Cited

U.S. PATENT DOCUMENTS

| | | | | |
|---|---|---|---|---|
| 5,270,542 | A | 12/1993 | McMurry et al. | |
| 5,382,794 | A | 1/1995 | Downey et al. | |
| 6,248,590 | B1 | 6/2001 | Malachowski | |
| 6,589,792 | B1 | 7/2003 | Malachowski | |
| 6,924,004 | B2 | 8/2005 | Rao et al. | |
| 7,361,891 | B2 * | 4/2008 | Gard | G01N 1/22 250/281 |
| 7,476,851 | B2 * | 1/2009 | Wang | G01N 1/2208 250/251 |
| 7,956,697 | B2 * | 6/2011 | Aoyama | H03L 7/26 331/3 |
| 8,049,185 | B2 | 11/2011 | Hayashi et al. | |
| 2009/0128810 | A1 | 5/2009 | Bates | |
| 2010/0110177 | A1 | 5/2010 | Yamada et al. | |
| 2013/0011930 | A1 | 1/2013 | Takegawa et al. | |

FOREIGN PATENT DOCUMENTS

| | | | |
|---|---|---|---|
| JP | 2008261737 | A | 10/2008 |
| JP | 2011503622 | A | 1/2011 |
| WO | 9944037 | A1 | 9/1999 |
| WO | 2009065062 | A1 | 5/2009 |
| WO | 2009096868 | A1 | 8/2009 |
| WO | 2011114587 | A1 | 9/2011 |

OTHER PUBLICATIONS

International Search Report (ISR) dated Dec. 10, 2013 issued in International Application No. PCT/JP2013/078138.

Extended European Search Report dated Jun. 30, 2016, issued in counterpart European Application No. 13860647.0.

Deng, et al., "Focusing Particles with Diameters of 1 to 10 Microns into Beams at Atmospheric Pressure", Aerosol Science and Technology, vol. 42, No. 11, Sep. 25, 2008, pp. 899-915.

Chreiner, et al.. "Focusing of Aerosol into a Particle Beam at Pressures from 10 to 150 Ton", Aerosol and Science Technology, vol. 31, Nov. 1, 1999, pp. 373-382.

* cited by examiner

3a

PARTICLE BEAM FORMING DEVICE

TECHNICAL FIELD

The present invention relates to a particle beam forming device suitable for analyzing atmospheric particulate matter (aerosols).

BACKGROUND ART

Interest in the health effects of atmospheric particulate matter (aerosols) has increased, and the development of devices for analyzing the composition and behavior thereof is being studied in various quarters.

Aerosol mass spectrometers have recently been developed as a device for analyzing particle components, and are being utilized in the compositional analysis of particulate matter in the atmosphere and other environments. An aerosol mass spectrometer is a device for taking in a gas comprising particles inside a vacuum chamber from a space to be assessed, and measuring particle composition by collecting and thermally vaporizing the particles. In an aerosol mass spectrometer of this type, particles must be guided into a vacuum chamber, and these particles must be collected in a collection/thermal vaporization unit inside the chamber. As means for achieving this, for example, particle beam forming means such as that illustrated in FIG. 16 is used (refer to Patent Document 1). This particle beam forming means 100 comprises a prefocusing structure 114 having an internal orifice structure, and a tubular structure 118 having at least one primary focusing means 120 for forming a particle beam downstream from the prefocusing structure. The tubular structure 118 captures gas-dispersed particles from a particle source 112, and a particle flow is linearly formed by flow control in accordance with the internal prefocusing structure 114 and primary focusing means 120. That is, a gas component 112*a* having a higher lateral diffusion rate than the particles 112*b* is retained inside the tubular structure 118 and a vacuum chamber 132 and evacuated via an exhaust port 134 of the vacuum chamber 132, while the particles 112*b* maintain straight-line mobility and are ejected as a particle beam from a hole disposed in a partition 130 of the vacuum chamber 132. Particles are collected by causing this particle beam to collide with a collector disposed in a mass spectrometry unit, and the particles are thermally vaporized and guided to a detector, thereby making mass spectrometry of atmospheric particles possible, and enabling the analysis of the chemical composition of the particles.

This technology is not merely directed toward analyzing the chemical composition of particles; it is also used in semiconductor manufacturing and other such fields. For example, in Patent Document 2, a nanoparticle-containing gas for modifying the surface of a semiconductor is sprayed and specific particles are deposited onto a semiconductor substrate using the technology of Patent Document 1 to change the functionality and properties thereof. Technology for introducing such particles into a chamber (vacuum) and allowing them to converge within a certain range is of prime importance in measuring and manufacturing technologies.

PRIOR ART DOCUMENTS

Patent Documents

[Patent Document 1] U.S. Pat. No. 5,270,542
[Patent Document 2] U.S. Pat. No. 6,924,004

DISCLOSURE OF THE INVENTION

Problems to be Solved by the Invention

For particle beam forming means like that illustrated in FIG. 16, the description is such that the particle beam does not spread out laterally relative to the direction of travel, but in point of fact, the particle beam is injected having a lateral spread relative to the direction of travel. This spread constitutes a conical shape with the injection position at the top, and as such, depending on the location and size of the collector, there is the likelihood that not all of the particles introduced will be collected. When applied to semiconductor manufacturing as in Patent Document 2, since the spatial distribution of the particle beam cannot be ascertained, it is impossible to control the amount of introduced particles that are deposited, and this is believed to give rise to the problem of reduced manufacturing yields.

With the foregoing problems in view, an object of the present invention is to provide a particle beam forming device that is capable of forming a particle beam, and evaluating and controlling the spatial distribution of the formed particle beam.

Means to Solve the Problems

To achieve the above-stated object, a particle beam forming device of the present invention is a particle beam forming device for forming either a linear or conical particle beam from a particle source in which particles are dispersed in a gas, characterized by comprising: a reduced-pressure vessel in which pressure is reduced; particle beam generating means, which has one end arranged outside of the reduced-pressure vessel and the other end arranged inside the reduced-pressure vessel, and which captures the particle source from outside the reduced-pressure vessel and introduces the particle beam into the reduced-pressure vessel; and particle beam evaluating means for evaluating a spatial distribution of the particle beam inside the reduced-pressure vessel.

In the present invention, it is preferable that the particle beam evaluating means be provided with: light directing means for directing light on the particle beam; light-scattering detection means for detecting scattered light generated when the light that has been directed on the particle beam hits the particles; and signal processing means for recording and processing a signal outputted from the light-scattering detection means in accordance with an intensity and/or a frequency of detection of the scattered light.

It is preferable that the signal processing means calculate a spatial spread of the particle beam based on an intensity-spanning frequency distribution and/or a pulse width-spanning frequency distribution of the scattered light, and the relationship between a predetermined spatial intensity of the light and the spatial spread of the particle beam.

It is preferable that the signal processing means calculate the spatial spread of the particle beam at a plurality of locations following the direction of travel of the particle beam on the basis of signals from the plurality of locations, and calculate a spread angle of the particle beam from the spatial spread at each location.

It is preferable that the present invention have means for adjusting the spatial distribution of the particle beam on the basis of the spatial spread and/or spread angle of the particle beam determined by the signal processing means.

It is preferable that the particle beam generating means comprise a device for emitting particles through the particle source in either a linear or conical shape inside a tubular structure provided with a focusing mechanism provided upright therein.

It is preferable that the configuration be such that the reduced-pressure vessel is divided into an upstream exhaust chamber in which the particle beam generating means is arranged and a downstream exhaust chamber in which the particle beam evaluating means is arranged, a skimmer, which comprises a substantially conical through-hole through which the particle beam passes, the narrow opening thereof disposed on said upstream exhaust chamber side, is disposed in a partition separating the exhaust chambers, and the downstream exhaust chamber is at a lower pressure than the upstream exhaust chamber so as to enable exhausting to be performed respectively therefrom.

It is preferable that the downstream exhaust chamber be provided with an output port for extracting the particle beam from the downstream exhaust chamber.

It is preferable that the light directing means have laser light generating means, and a light-transmitting window disposed in the reduced-pressure vessel, and adapted to transmit the laser light directed by the laser light generating means.

It is preferable that the light directing means and the light-scattering detection means be disposed in a plurality of locations at a prescribed spacing in the reduced-pressure vessel following the direction of travel of the particle beam.

It is preferable that the means for adjusting the spatial distribution of the particle beam include at least one means selected from the group consisting of: means for adjusting the length in a path that the particle beam travels of the downstream exhaust chamber of the reduced-pressure vessel; means for adjusting the angle of the downstream exhaust chamber relative to the upstream exhaust chamber; and means for adjusting the angle of the particle generating means relative to the upstream exhaust chamber.

Advantageous Effects of the Invention

According to the particle beam forming device of the present invention, since particle beam evaluating means for evaluating the spatial distribution of a particle beam is provided, trapping efficiency when analyzing particles and the accuracy of delivering particles to a target range can be easily evaluated each time a particle beam has been formed without interfering with the particle beam.

Furthermore, by providing light directing means, light-scattering detection means, and signal processing means as particle beam evaluating means, scattered light produced when light directed on the particle beam hits the particles can be detected, a signal corresponding to the intensity and/or frequency of detection of the scattered light can be captured as a physical representation of the spatial distribution of the particle beam, and the spatial spread and spread angle of the particle beam can be accurately evaluated.

Also, by further providing means for adjusting the spatial distribution of the particle beam, it becomes possible to control particle beam formation in accordance with the spatial distribution of the particle beam.

BRIEF DESCRIPTION OF THE DRAWINGS

FIG. 15B is an example of when the directed light is substantially larger than the distribution range of the particle beam.

BEST MODE FOR CARRYING OUT THE INVENTION

The present invention will be described in detail below while referring to the accompanying drawings.

Figure 1:
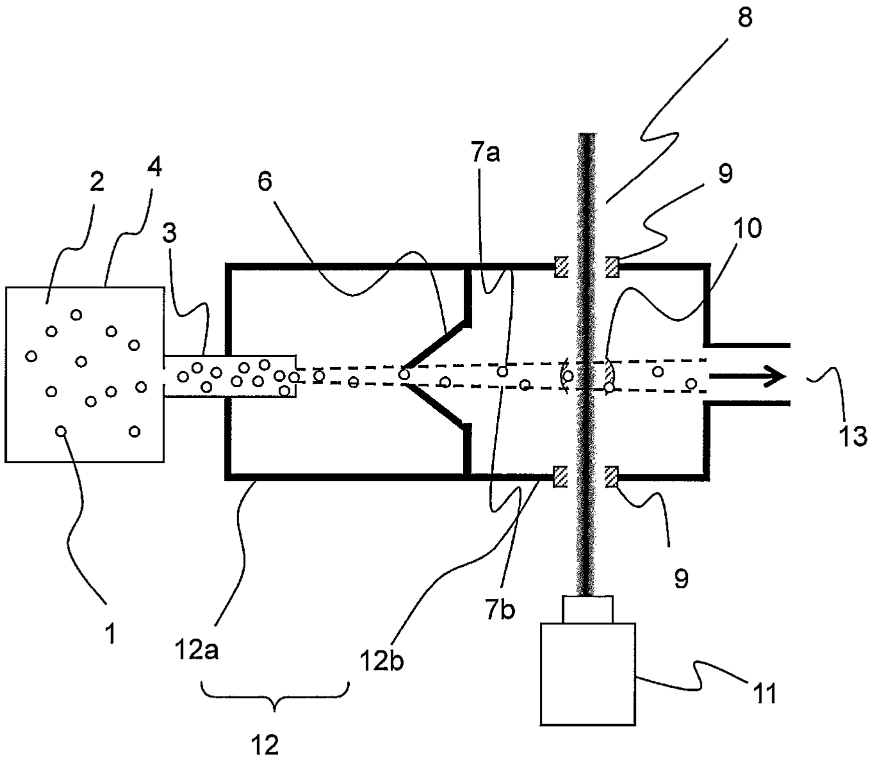
FIG. 1 is a plan view of an overview of the configuration of a particle beam forming device pertaining to a first embodiment of the present invention.

A first embodiment of the present invention will be described first. FIG. 1 is a plan view of an overview of the configuration of a particle beam forming device pertaining to the first embodiment of the present invention, and FIG. 2 is a side view thereof.

Figure 2:
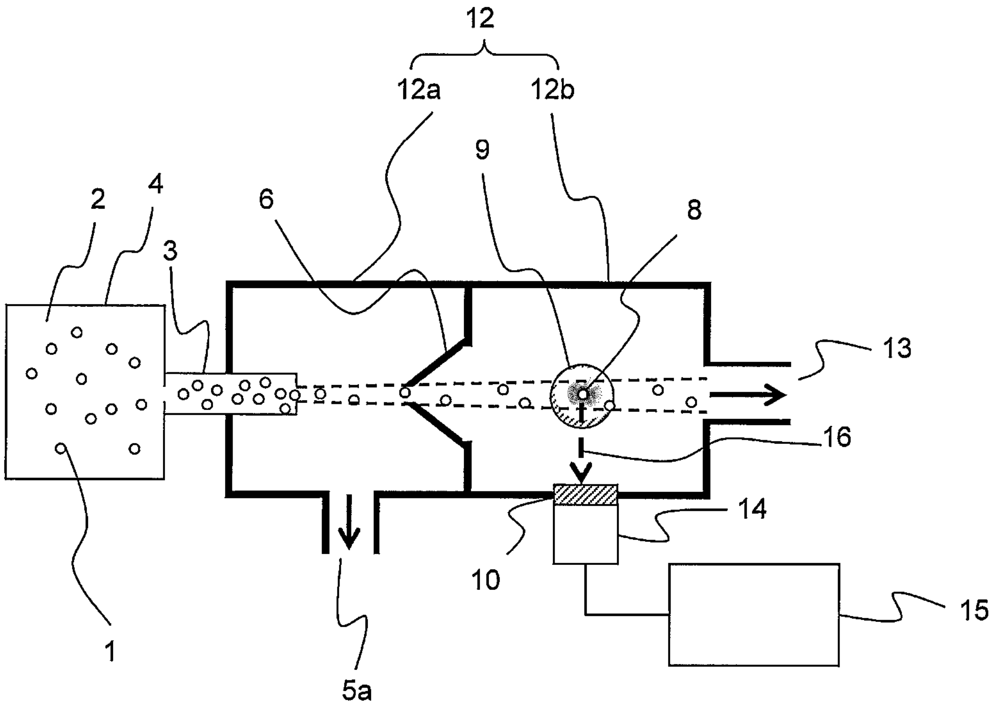
FIG. 2 is a side view of an overview of the configuration of a particle beam forming device pertaining to a first embodiment of the present invention.

As illustrated in FIGS. 1 and 2, the particle beam forming device pertaining to this embodiment comprises particle beam generating means 3, a reduced-pressure vessel 12, laser light generating means 11, light-scattering detection means 14, and signal processing means 15.

In the present aspect, the particle beam generating means 3 assumes a tubular structure, and passes through a side wall of the reduced-pressure vessel 12 so as not to impair the pressure-reducing mechanism thereof. Then, being configured such that one end is arranged outside of the reduced-pressure vessel 12 and the other end is arranged inside the reduced-pressure vessel 12, the particle beam generating means 3 captures a particle source 2 from outside the reduced-pressure vessel 12 and introduces a beam of particles 1 into the reduced-pressure vessel 12. The particle source 2 may be a source of particles in which particles are dispersed in a gas, and, for example, may without limitation include ambient air, a nanoparticle-containing gas for modifying the surface of a semiconductor, laboratory-prepared monodisperse-particle-containing air, and particles inside a pressure vessel. The particle source 2 may be continuously supplied, intermittently supplied, or successively supplied to the particle beam generating means 3. The particle source 2 may also be supplied to the particle beam generating means 3 after a target concentration of particles has reached a desired range by diluting the particle source 2 with cleaned air, or by adjusting the pressure inside a storage container 4 for storing the particle source 2.

In the present aspect, the reduced-pressure vessel 12 is divided into an upstream exhaust chamber 12*a* in which the particle beam generating means 3 is arranged, and a downstream exhaust chamber 12*b* separated therefrom by a partition. Then for a particle source 2 at, e.g., atmospheric pressure, the pressure in the upstream exhaust chamber 12*a* is reduced to around $10^{-3}$ Torr by an exhaust device (not shown) communicating with an exhaust port 5*a*, and the pressure in the downstream exhaust chamber 12*b* is reduced to a relatively high vacuum of around $10^{-5}$ Torr by an exhaust device (not shown) communicating with an exhaust port 13, thus giving rise to differential pumping, whereupon the particles 1 are guided from the particle beam generating means 3 to the upstream exhaust chamber 12*a* and then to the downstream exhaust chamber 12*b*. The flow of these particles 1 is formed on the same axis as the tubular structure comprising the particle beam generating means 3. Hereinafter, the direction of flow of particles on this same axis will be called the direction of travel of the particle beam. Furthermore, the exhaust port 13 of the downstream exhaust chamber 12*b* also serves as an output port for extracting the particle beam from the downstream exhaust chamber 12*b*.

Ideally, the particle beam generating means 3 forms a linear particle beam, but in actuality the emitted particle beam is distributed inside the reduced-pressure vessel 12 having a conical spatial spread bounded by the upper limit 7*a* and lower limit 7*b* of FIG. 1. That is, the particles emitted from the output port of the laser beam generating means 3 have a velocity component other than the direction of travel of the particle beam comprising the particles, while a carrier gas, which is the driving source of the particles, applies viscosity and other such forces to the particles 1 in a diffusion process inside the vessel, thereby gradually diffusing the particles 1 at right angles to the direction of travel to form a particle beam having a conical spatial spread.

In the present aspect, a skimmer 6 comprising a substantially conical through-hole with the narrow opening on the upstream exhaust chamber 12*a* side is provided in the partition that separates the upstream exhaust chamber 12*a* and downstream exhaust chamber 12*b* in the reduced-pressure vessel 12. A particle beam is introduced into the downstream exhaust chamber 12*b* from the upstream exhaust chamber 12*a* through the skimmer 6. The shape of the skimmer 6 aids in efficiently exhausting the carrier gas in which the particle beam is intermixed. That is, since the particle beam includes gas molecules, the gas, which has a greater diffusion velocity laterally from the direction of travel than the particles, is selectively removed, enabling the particles, which alternatively have a smaller diffusion velocity laterally from the direction of travel than the gas molecules, to selectively pass through the skimmer 6. Also, the pressure difference between the upstream exhaust chamber 12*a* and the downstream exhaust chamber 12*b* is maintained by the sufficiently large surface area of the partition relative to the diameter of the skimmer 6. Thus, since the skimmer has the effect of greatly changing the properties of the particle beam in accordance with the shape thereof, it is preferable to be a structure that enables the skimmer to be replaced with one of a different shape.

Figure 3:
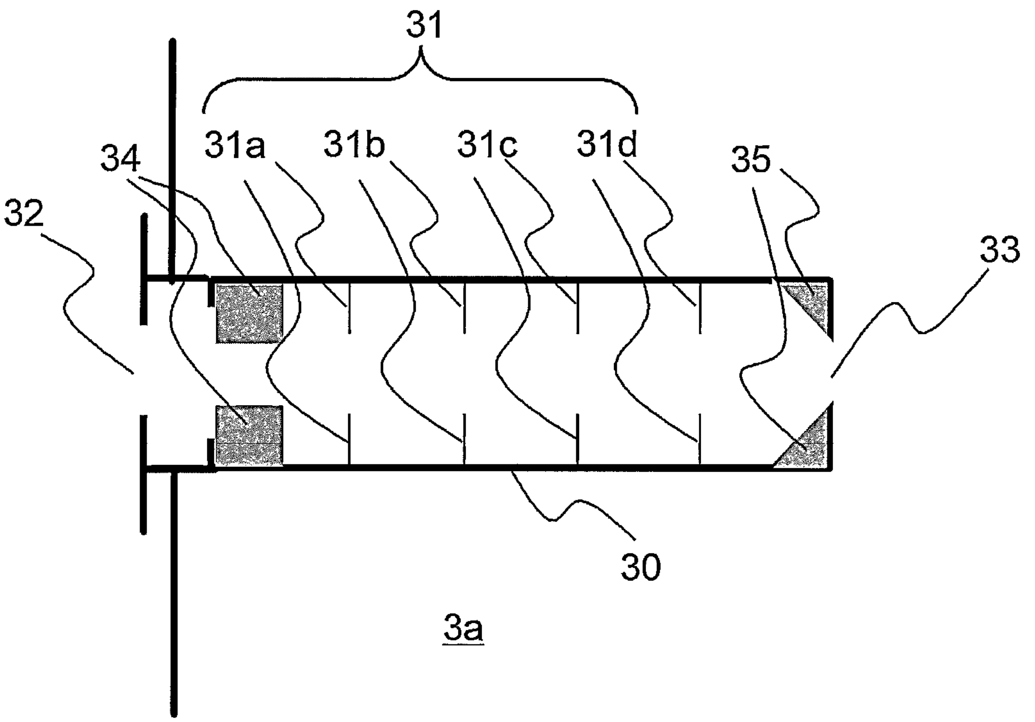
FIG. 3 shows a schematic diagram of an aerodynamic lens given as one example of particle beam generating means 3.

FIG. 3 shows a schematic diagram of an aerodynamic lens as an example of the particle beam generating means 3. This aerodynamic lens 3*a* constitutes a structure that provides a focusing mechanism provided upright on the inner side of the inside of a tubular structure, and emits particles through the particle source in either a linear or conical shape inside this tubular structure. That is, as illustrated in FIG. 3, the structure is such that several stages of orifices 31*a* through *d* are arranged inside of a tubular housing 30, on the side of one end thereof is disposed an entry port 32 through which a particle source flows in, and on the side of the other end thereof is disposed an exit port 33 through which a particle beam of particles is emitted. In this drawing, the entry port 32 is arranged on the particle source 2 side, and the exit port 33 is arranged on the reduced-pressure vessel 12 side. The particle source flows in through the entry port 32 in accordance with the pressure difference, and when the particle source passes through the aerodynamic lens, whereas the particle carrier gas is diffusing as it moves and the linear movement thereof is impeded by the orifices 31, the particles, which comprise either solids or liquids, have higher straight line stability than the gas molecules, and therefore the movement of the particles that pass through the first-stage orifice 31*a* is not greatly impeded by the second stage and subsequent orifices 31*b* through *d*, the particles converge into a beam shape, and a particle beam is emitted on the reduced-pressure vessel 12 side through the exit port 33. Also, in the present aspect of the aerodynamic lens 3*a*, a nozzle 34 is provided in the entry port 32, and a nozzle 35 is provided in the exit port 33, allowing the further convergence of the particle beam.

Figure 4:
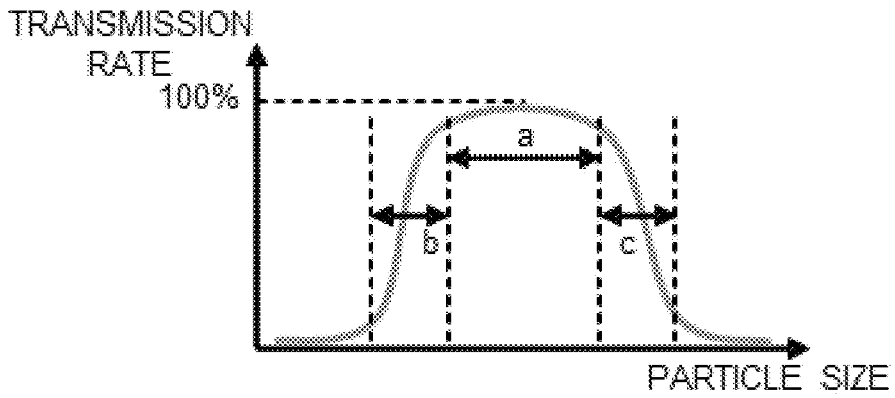
FIG. 4 is a graph illustrating the relationship between the size of a particle and the transmission rate of the particle in the particle beam generating means.

Generally speaking, a particle beam generating means having a structure such as that described above has transmission characteristics that are dependent on the size of the particles as illustrated in FIG. 4. That is, whereas there is a range of particle sizes that substantially 100% pass through the particle beam generating means as is indicated by region a in FIG. 4, particles on the fine particle size side and the coarse particle size side have difficulty passing through the particle beam generating means. In particular, the relative velocity of particles with respect to the carrier gas in the range of particle sizes indicated by region b in FIG. 4 and the range of particle sizes indicated by region c in FIG. 4 determines the convergence of the particle beam. Accordingly, for these ranges of particle sizes, it is possible to control the convergence of the particle beam by adjusting the pressure inside the particle beam generating means. That is, for example, when the particles to be introduced are in the range of particle sizes indicated by region b in FIG. 4, the lateral distribution relative to the direction of travel of the particle beam can be minimized by lowering the pressure inside the particle beam generating means (that is, the convergence of the particle beam increases, and the spread angle decreases). Alternatively, when the particles to be introduced are in the range of particle sizes indicated by region c in FIG. 4, the convergence of the particle beam can be improved by increasing the pressure inside the particle beam generating means. The pressure inside the particle beam generating means 3 can be adjusted in accordance with the structure and size of the nozzles 34 and 35, or the number of orifices and/or the spacing between the orifices 31 in the aerodynamic lens 3*a* illustrated in FIG. 3 described hereinabove. It is also possible to change the transmission characteristics that are dependent on the size of the particles by changing the fluid flow inside the particle beam generating means 3. Thus, because of an effect by which the shape of the particle beam generating means greatly changes the properties of the particle beam, it is preferable to be a structure that enables the particle beam generating means to be replaced with one having a different shape.

Alternatively, in a case where the particles to be introduced are in the range of particle sizes indicated by region a in FIG. 4, generally speaking, the convergence thereof results in a lateral distribution relative to the direction of travel of the particle beam within a range of around an 1-mm radius (a spread angle of around 1 mrad) when the length of the particle beam path is around 1 m.

As described hereinabove, the range of particle sizes capable of generating a particle beam also depends of the structure of the particle beam generating means, and normally refers to particles having an aerodynamic diameter of between 0.01 and 100 μm, and more typically of between 0.01 and 10 μm, and most typically of between 0.1 and 3 μm. The particle beam generating means is not limited to a method using the aerodynamic lens mechanism illustrated in FIG. 3 described above, and, for example, a capillary inlet method (Murphy and Sears, "Production of Particle Beams," Journal of Applied Physics, 1964, No. 35, pp. 1986-1987) can be cited.

In the present aspect, as illustrated in FIG. 1, light-transmitting windows 9 through which a laser light 8 from laser light generating means 11 passes, are provided in both sidewalls of the downstream exhaust chamber 12*b* of the reduced-pressure vessel 12, and a laser light 8 is directed from a substantially perpendicular direction relative to the direction of travel of the particle beam. Then, the directed laser light 8 passes through the light-transmitting window 9 provided in the downstream exhaust chamber 12*b* sidewall on the opposite side of the directing side so as not to be reflected. As illustrated in FIG. 2, a light collection optical system (a condensing lens) 10 is arranged in another sidewall of the downstream exhaust chamber 12*b* of the reduced-pressure vessel 12, and this condenses scattered light 16 from the particles so as to enable the scattered light to be detected by light-scattering detection means 14 that is integrated with the condensing lens 10. In addition, a signal processing means 15 for recording and processing a signal outputted from the light-scattering detection means 14 is installed outside the reduced-pressure vessel 12 due to problems related to vacuum-resistance and heat-resistance properties, while being as the laser light generating means 11 and the light-scattering detection means 14.

The particle beam introduced from the particle source through the particle beam generating means 3 travels inside the upstream exhaust chamber 12*a*, exits the skimmer 6, and is introduced into the downstream exhaust chamber 12*b*, where it is subjected to a laser light 8 from the laser light generating means 11 introduced via the light-transmitting window 9 in a prescribed detection region provided midway through the travel thereof. The laser light 8 hits the particles 1 comprising the particle beam, generating scattered light 16. If the particles 1 are regarded here as being of a range of sizes capable of being detected in accordance with Mie scattering, the scattered light intensity has a prescribed relationship with the intensity of the directed light and the wavelength of the directed light. As in a case where a standard particle having a known particle size, for example, a polystyrene latex (PSL) is used, or a case where the introduced particles are classified using an electrical classifier or the like in which the size of the particles 1 is considered to be fixed, when a light such as a laser light that can be regarded to have the wavelength and spatial intensity distribution fixed is used as the directed light, the scattered light 16 condensed by the light collection optical system 10 is generally detected in the detection means 14 at a fixed intensity.

There are no particular limitations on the directed light that is used, but, for example, a 660-nm or 532-nm laser light with a relatively large output is preferable for measuring the spatial distribution on the fine particle size side (particle size of around 0.1 to 0.5 μm). The laser light generating means 11, for example, can be a semiconductor laser, a solid-state laser, or a gas laser. Also, as will be described below, a light having a known spatial intensity distribution is preferable for evaluating the spatial distribution of a particle beam. A laser light with a fixed intensity distribution can be generated using conventional methods in accordance with a lens-based beam forming method (a beam homogenizer or laser line generator) or a mirror-based beam forming method (a deformable mirror). Also, since it is possible if the intensity distribution is known, for example, it is also possible to use a laser light with a Gaussian distribution formed using the aforementioned semiconductor laser, solid-state laser, or gas laser.

Figure 5:
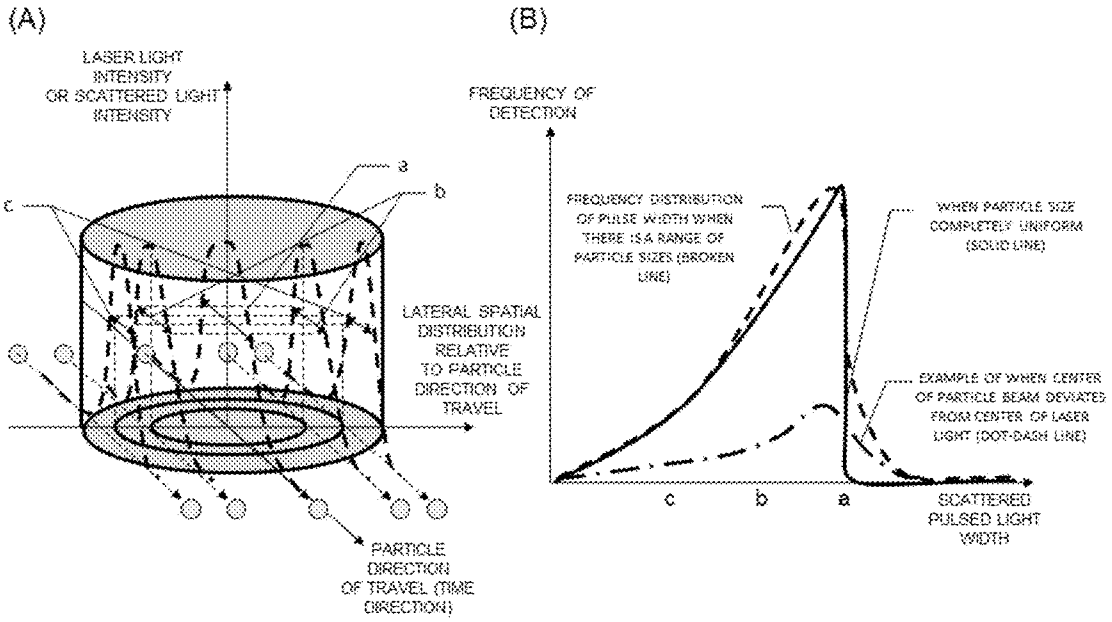
FIG. 5 is an example of observation results when a laser light, which is regarded to have the spatial intensity distribution fixed at a prescribed range, is directed on a particle beam, FIG. 5A being a conceptual illustration of the direction of travel of the particle beam when viewed from obliquely above, and FIG. 5B being a graph illustrating an example of a frequency distribution for the pulse width of the scattered light.

FIG. 5 gives an example of observation results when a laser light, which is regarded to have the spatial intensity distribution fixed, is directed on a particle beam. This example refers to a case in which the centers of the laser light and the particle beam coincide with one another, and, in addition, the introduced particles are of a single particle size. FIG. 5A is a conceptual illustration thereof, and FIG. 5B is a graph illustrating an example of the frequency distribution of the pulse width of the scattered light when the pulse width of the scattered light detected for each particle is represented on the X axis, and the frequency of detection thereof is represented on the Y axis.

As illustrated in FIG. 5A, the spatial intensity distribution of the laser light exhibits a uniform distribution when viewed as a cross-section of the direction of travel of the laser light. Then, scattered light is generated by a particle that intersects the laser light from a substantially perpendicular direction. At this time, as illustrated in FIGS. 5A and B, the particle that passes through the center of the laser light (indicated by a in FIG. 5A) generates scattered light having the largest pulse width, and particles like this are distributed in the region indicated by a in FIG. 5B. On the one hand, a particle that passes through the middle widthwise of the beam radius of the laser light (indicated by b in FIG. 5A) generates scattered light having an intermediate pulse width, and particles like this are distributed in the region indicated by b in FIG. 5B. On the other hand, a particle that passes through in close proximity to the boundary of the beam radius of the laser light (indicated by c in FIG. 5A) generates scattered light having the smallest pulse width, and particles like this are distributed in the region indicated by c in FIG. 5B. In a case where the spatial distribution of a concentration of particles in the particle beam constitutes a Gaussian-shaped distribution having the center of the particle beam as the apex, a frequency distribution of the pulse width of the scattered light like that of the solid line in FIG. 5B is obtained. Also, in a case where the particle size is not fixed and there is a certain range of sizes, this range of sizes will manifest itself as differences in travel time, and as such, a frequency distribution of the pulse width of the scattered light like that of the broken line in FIG. 5B is obtained. Alternatively, in a case where the center of the particle beam and the center of the laser light differ, for example, a frequency distribution of the pulse width of the scattered light like that of the dot-dash line in FIG. 5B is obtained.

Figure 6:
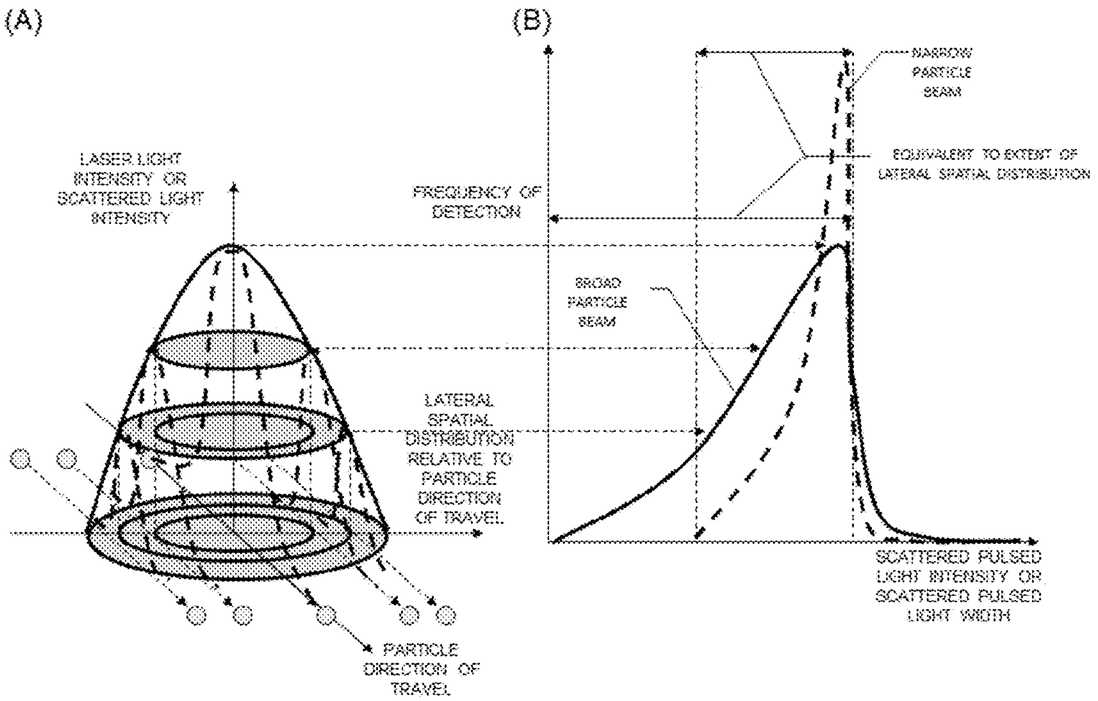
FIG. 6 is an example of observation results when a laser light, having a Gaussian distribution as a spatial intensity distribution, is directed on a particle beam, FIG. 6A being a conceptual illustration of the direction of travel of the particle beam when viewed from obliquely above, and FIG. 6B being a graph illustrating an example of a frequency distribution for the scattered light intensity (or pulse width)

FIG. 6 gives an example of observation results when a laser light having a Gaussian distribution as a spatial intensity distribution is directed on a particle beam. This example pertains to a case in which the centers of the laser light and the particle beam coincide with one another, and, in addition, the introduced particles are of a single particle size. FIG. 6A is a conceptual illustration thereof, and FIG. 6B is a graph illustrating an example of the frequency distribution of the scattered light intensity (or pulse width) detected for each particle.

Figure 7:
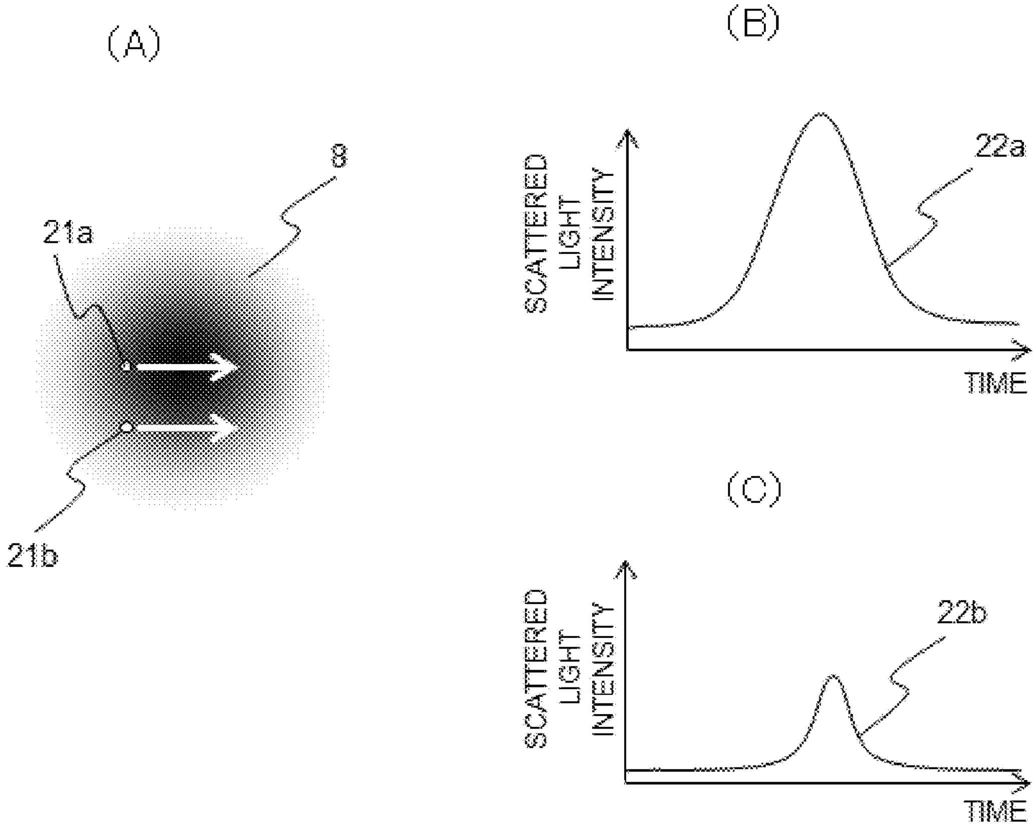
FIG. 7 is an example of observation results when a laser light, having a Gaussian distribution as a spatial intensity distribution, is directed on a particle beam, FIG. 7A being a conceptual illustration of the laser light when viewed from the direction of illumination, and FIGS. 7B and 7C being graphs illustrating examples of scattered light pulses detected in each of particles.

As illustrated in FIG. 6A, the spatial intensity distribution of the laser light exhibits a Gaussian distribution when viewed as a cross-section of the direction of travel of the laser light. Then, as illustrated in FIG. 5 described above, scattered light is generated by a particle that intersects the laser light from a substantially perpendicular direction. At this time, as illustrated in FIGS. 7A, B, and C, the scattered light intensity from a particle 21*a* that passes through in proximity to the center (FIG. 7A) is large in terms of time and intensity like 22*a* (FIG. 7B), and a particle 21*b* that passes through a space that deviates from the center of the laser light 8 (FIG. 7A) is small in terms of time and intensity relative to 22*a* like 22*b* (FIG. 7C). Therefore, frequency distributions like those of FIG. 6B are obtained when either the scattered light intensity or pulse width serves as the X axis.

In addition, the configuration may be such that lasers of a plurality of types of wavelengths are generated by the laser light generating means 11, the laser light is guided from the light-transmitting window 9 and directed on the particle beam, an optical filter is provided on the light-scattering detection means 14 side, and scattered light is detected for each wavelength. In so doing, it also becomes possible to evaluate the spatial distribution of a particle beam from a particle source having a plurality of particle sizes and compositions such as ambient air.

For example, the following can be performed to evaluate the spatial distribution of a particle beam based on the frequency distribution of the scattered light intensity (or pulse width) obtained as described hereinabove.

(1) In a case where a plurality of observation results are compared under differing conditions, when, as in the graph illustrated by the broken line in FIG. 6B, there is a sharper rise than in the graph illustrated by the solid line in FIG. 6B, and the maximum value of the frequency is also relatively high, the particle beam represented in the graph illustrated by the broken line in FIG. 6B can be evaluated as being a particle beam having a smaller lateral spatial spread relative to the direction of travel of the particle beam than the particle beam represented in the graph illustrated by the solid line in FIG. 6B.

(2) When the size of an introduced particle can be predicted, the relation between the particle beam spread and a detection signal can be estimated from the spatial distribution of the laser light and a predicted particle beam distribution (for example, a Gaussian-shaped distribution in which the spatial distribution of a concentration of particles in the particle beam has the center of the particle beam as the apex), and the spread of this particle beam can be inferred by comparing this estimate to an actual measurement. Also, in a case where the travel velocity is known using a fluid calculation and/or a fifth embodiment described below, the pulse width of the scattered light can be estimated from the width and velocity of the laser light when the center of the particle beam passes through the center of the laser light, and therefore, an evaluation can be made such that when the pulse width of the maximum frequency at which a pulse is detected is more or less the same as the estimated value thereof, the particle beam is distributed in the center of the directed light, and when the pulse width is narrower than the estimated value, the particle beam is distributed in a portion offset from the center of the laser light.

Furthermore, in order to confirm the reliability of evaluations such as those described hereinabove via experimentation, a method for determining the actual spatial spread of a particle beam using a particle having prescribed characteristics (a model particle, for example, PSL) is given. A concrete example of this will be described below.

Next, a second embodiment of the present invention will be described.

Figure 8:
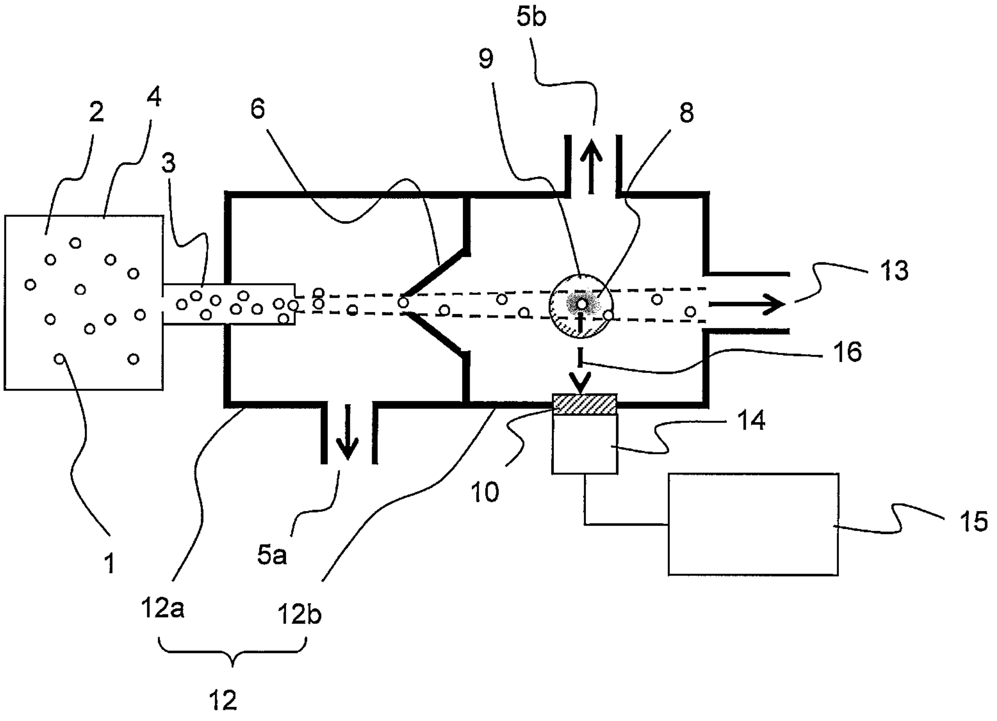
FIG. 8 is a side view of an overview of the configuration of a particle beam forming device pertaining to a second embodiment of the present invention.

FIG. 8 shows a side view of an overview of the configuration of a particle beam forming device pertaining to a second embodiment of the present invention. Since the particle source 2, the particle beam generating means 3, the skimmer 6, the laser light generating means 11, the laser light 8, the light-transmitting window 9, the light collection optical system 10, the light-scattering detection means 14, the scattered light 16, and the signal processing means 15 are the same as those in the first embodiment, the same reference symbols have been assigned, and descriptions thereof will be omitted. Descriptions of the respective embodiments hereinbelow will also be omitted in similar fashion.

In the present aspect, in addition to the first embodiment described above, an exhaust port 5*b* separate from the exhaust port 13 that also serves as the particle beam output port is disposed in the downstream exhaust chamber 12*b*. The pressure in the downstream exhaust chamber 12*b* can be adjusted by an exhaust device (not shown) communicating with the exhaust port 5*b*. When introducing a particle beam into a different vessel further downstream through the exhaust port 13 that also serves as the particle beam output port, this makes it possible to adequately exhaust the pressure through the exhaust port 5*b* even though the particle beam output port (exhaust port 13) has been made intentionally narrow for the purpose of narrowing the particle beam.

Next, a third embodiment of the present invention will be described.

Figure 9:
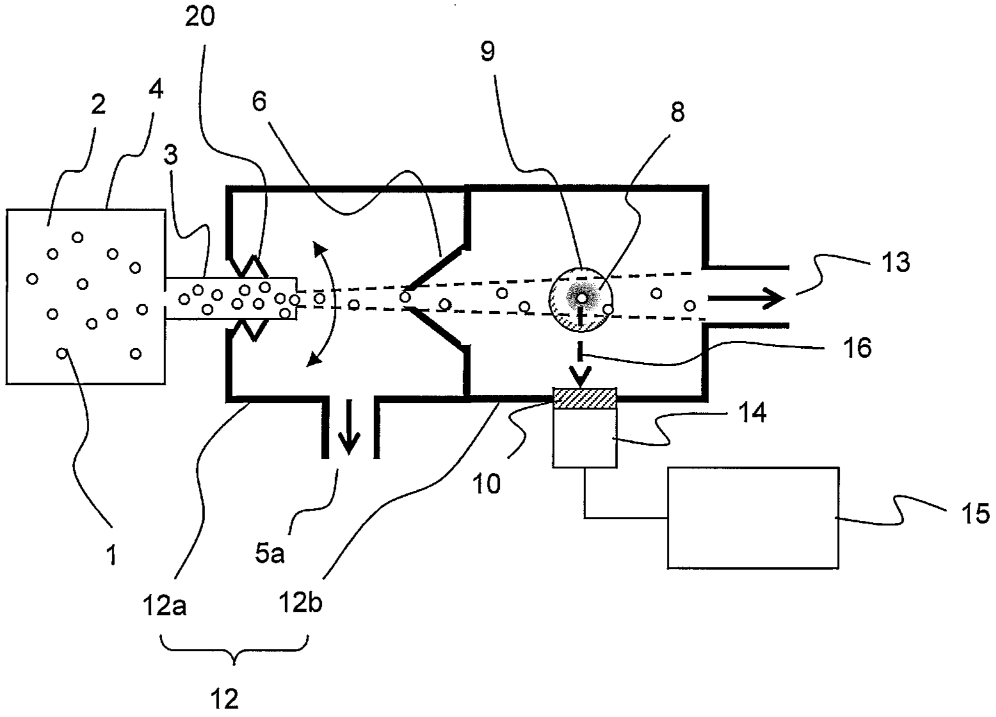
FIG. 9 is a side view of an overview of the configuration of a particle beam forming device pertaining to a third embodiment of the present invention.

FIG. 9 shows a side view of an overview of the configuration of a particle beam forming device pertaining to a third embodiment of the present invention.

In the present aspect, in addition to the first embodiment described hereinabove, means for adjusting the angle of the particle beam generating means 3 relative to the upstream exhaust chamber 12a is provided in the upstream exhaust chamber 12a. As a specific configuration, for example, a mechanism capable of changing the angle while maintaining air-tightness using a bellows 20 or the like at the part where the particle beam generating means 3 and the upstream exhaust chamber 12a couple together is given. Then, based on the particle beam spatial spread and/or spread angle calculated by the signal processing means 15, it becomes possible to change the aforementioned angle. This makes it possible to adjust the relative angle of the direction of injection of a particle beam with respect to the upstream exhaust chamber and introduce the particle beam from the skimmer 6 into a path that connects with a detection region even when the direction of travel of the particle beam in accordance with the structure of the particle beam generating means 3 does not coincide with the coaxial direction of the particle beam generating means 3.

Next, a fourth embodiment of the present invention will be described.

Figure 10:
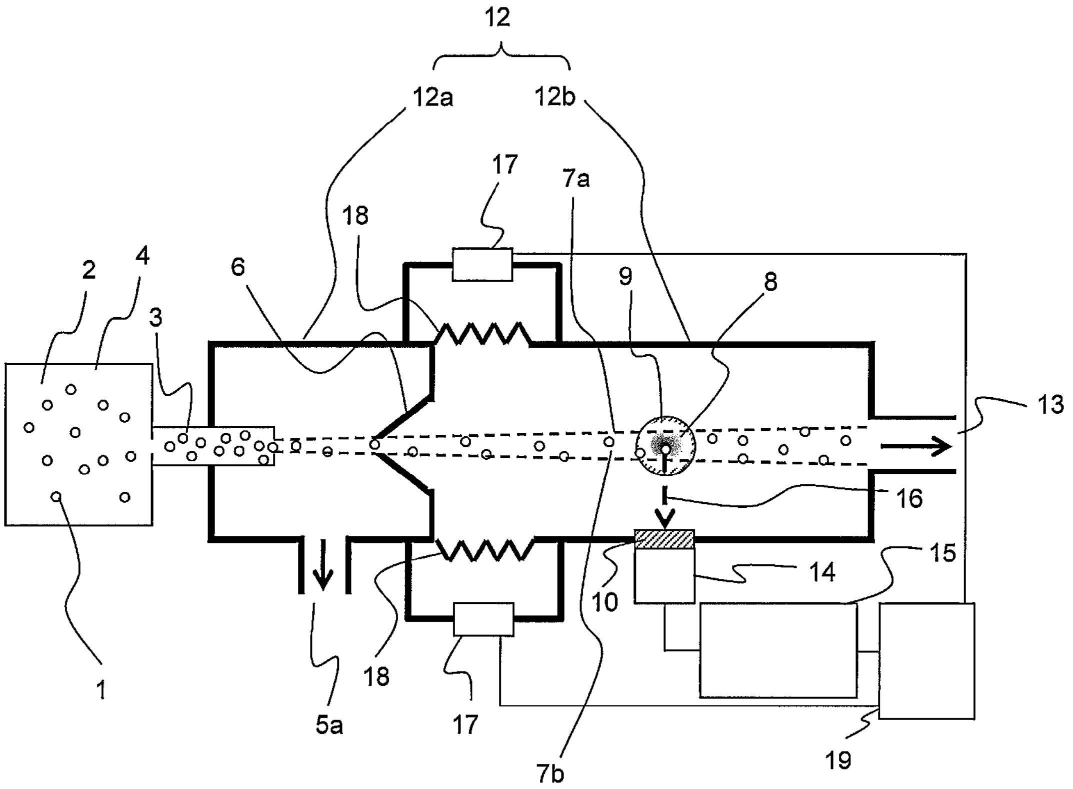
FIG. 10 is a side view of an overview of the configuration of a particle beam forming device pertaining to a fourth embodiment of the present invention.

FIG. 10 shows a side view of an overview of the configuration of a particle beam forming device pertaining to a fourth embodiment of the present invention.

In the present aspect, in addition to the first embodiment described hereinabove, means for adjusting the length of the downstream exhaust chamber 12b in the direction of travel of the particle beam is provided. As a specific configuration, for example, a mechanism for installing an actuator 17 and a bellows 18 in a sidewall of the downstream exhaust chamber 12b closer to the partition separating the upstream exhaust chamber 12a than to the light collection optical system (condensing lens) 10 connected to the light-scattering detection means 14, and extending and contracting the length thereof in the direction of travel of the particle beam is given. Then, an extension/contraction device driver 19 for driving the actuator 17 can be driven to change the length of the downstream exhaust chamber 12b in the direction to travel of the particle beam based on the particle beam spatial spread and/or spread angle calculated by the signal processing means 15. As described hereinabove, since the particle beam emitted from the output port of the particle beam generating means 3 has a conical spatial spread, this makes it possible to adjust the spatial spread of the particle beam in the detection region by changing the distance from the output port in the direction of travel of the particle beam.

Also, based on the difference between the particle beam spatial spread calculated by the signal processing means 15 and a desired particle beam spatial spread, it is possible to make adjustments such that the desired spatial spread exists in the detection region by driving the extension/contraction device driver 19 for driving the actuator 17, and driving the actuator 17 until the difference is eliminated.

In addition, based on the relationship between the extension/contraction distance resulting from the actuator 17 and the particle beam spatial spread, it is possible to determine the spread angle of the particle beam (that is, the angle formed by the upper limit 7a and the lower limit 7b). That is, when, for example, the calculated value of the pre-extension/contraction particle beam spatial spread is y, after which the extension/contraction is changed by the actuator 17 by x, and the calculated value thereof obtained by determining the particle beam spatial spread once again is $y+y_1$, the spread angle θ can be provided by formula (1) below.

[Formula 1]

$$\theta = 2\arctan\frac{y_1}{2x} \tag{1}$$

This makes it possible to calculate the particle beam spatial spread inside the device at an arbitrary point on the particle beam, and to more accurately control the spatial spread of the particle beam.

Also, the aforementioned actuator 17 and bellows 18 also serve as means for adjusting the angle of the downstream exhaust chamber relative to the upstream exhaust chamber. That is, the aforementioned angle can be changed by controlling the extension and contraction of at least two actuators based on the particle beam spatial spread and/or spread angle calculated by the signal processing means 15. When further introducing the particle beam into another downstream chamber through the exhaust port 13 that also serves as the particle beam output port, this makes it possible to adjust the relative angle of the particle beam relative to the downstream exhaust chamber and introduce the particle beam into a path that leads to the particle beam output port (exhaust port 13) from the skimmer 6 even when the direction of travel of the particle beam does not coincide with the particle beam output port (exhaust port 13).

It is also possible to confirm that the width of the directed light directed on the particles is large enough for the particle beam. A specific example of a method for doing this will be described below.

Next, a fifth embodiment of the present invention will be described.

Figure 11:
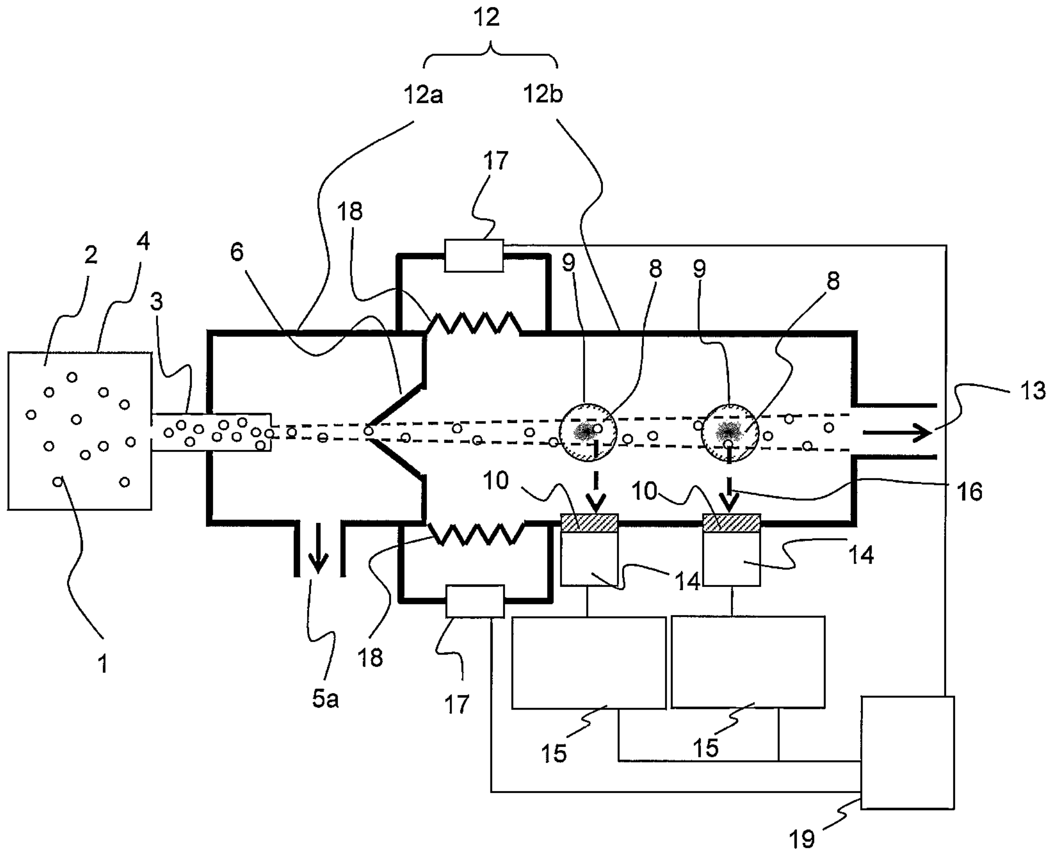
FIG. 11 is a side view of an overview of the configuration of a particle beam forming device pertaining to a fifth embodiment of the present invention.

FIG. 11 shows a side view of an overview of the configuration of a particle beam forming device pertaining to a fifth embodiment of the present invention.

In the present aspect, in addition to the fourth embodiment described hereinabove, at least two or more sets of a particle beam detection optical systems comprising the light collection optical system (condensing lens) 10, the light-scattering detection means 14, and the signal processing means 15 are provided in the downstream exhaust chamber 12b in the direction of travel of the particle beam. Then, the spatial spread of the particle beam in the detection region of a first particle beam detection optical system and the spatial spread of the particle beam in the detection region of a second particle beam detection optical system can be observed simultaneously. This makes it possible to determine the spread angle of the particle beam using the same method as that described for the above-described fourth embodiment based on the distance x between the first particle beam detection optical system and the second particle beam detection optical system in the direction of travel of the particle beam and the difference $y_1$ between the calculated values of the spatial spread of the particle beam in the detection regions of the first and the second particle beam detection optical systems, thus making it easier to determine the spatial spread of the particle beam at an arbitrary point in the chamber. Also, if the concentration of particles in the particle beam can be sufficiently reduced, it is possible to determine the particle velocity based on the travel time from the detection region of the first particle beam detection optical system to the detection region of the second particle beam detection optical system and the distance x between the first particle beam detection optical system and the second particle beam detection optical system in the direction of travel of the particle beam. This makes a more detailed particle beam evaluation possible.

First, second, third, fourth, and fifth embodiments have been described hereinabove, but the scope of the present invention is not limited thereto. Also, there are no particular limitations on combining, as appropriate, the configurations described in the respective embodiments, or combining configurations other than those as long as these combinations do not impair the operational advantage of the present invention.

The configuration may also be such that another chamber in which pressure has been reduced more than that of the downstream exhaust chamber 12*b* is disposed further downstream, a mechanism such as a mass spectrometer, a semiconductor manufacturing device, or an LCD manufacturing device is arranged inside this chamber, and a particle beam is introduced through the exhaust port 13 that also serves as the particle beam output port for compositional analysis and/or the modification of semiconductor materials. Such a mechanism may also be disposed inside the downstream exhaust chamber 12*b*.

[Method for Using Model Particle to Determine Actual Spatial Spread of Particle Beam in Detection Region in Advance]

As was described hereinabove, when the corresponding relationship between the actual spatial spread of the particle beam determined by using a model particle having characteristics approximating those of the particle to be introduced and frequency distribution of the scattered light intensity (or pulse width) observed by the light-scattering detection means 14 is acquired in advance, it is possible to determine the spatial distribution in the detection region from this corresponding relationship based on the frequency distribution obtained for a specific particle beam to be inspected.

In implementing the aforementioned method, there can be cited, as an example of a method for determining the actual spatial spread of the particle beam in a detection region using a model particle, a method comprising preparing a target in the detection region, introducing colored model particles (colored PSL) of a prescribed size or dye molecules obtained by particlizing 0.25-μm methyl orange or nigrosine classified by an electrical classifier, causing the particle beam to impinge on the target, recovering the target, and evaluating the range of the coloration either visually or using an optical microscope.

Figure 12:
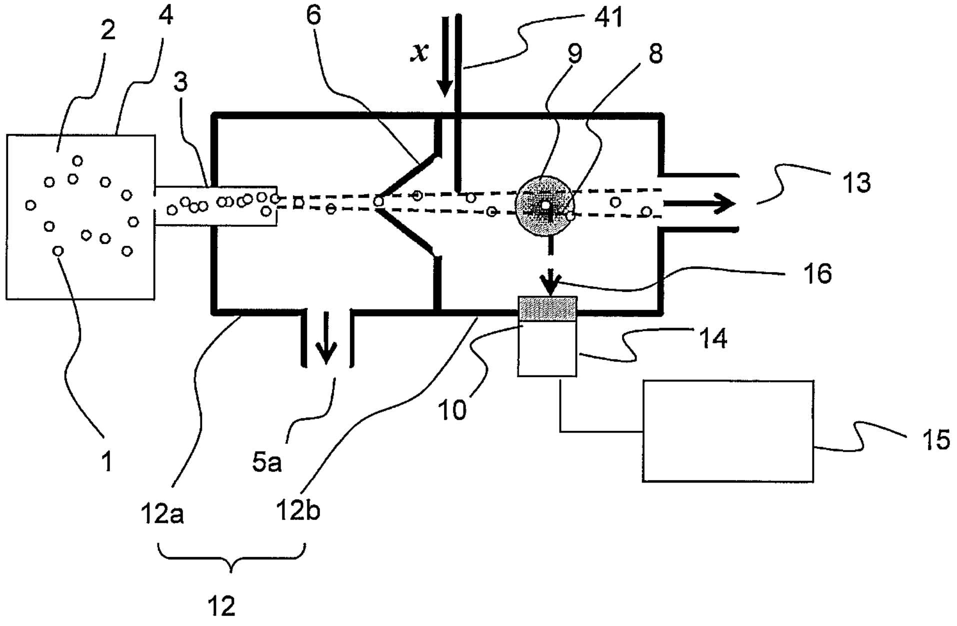
FIG. 12 is an illustration of a method for making a value to a spatial distribution of a particle beam relative to the direction of travel of the particle beam in accordance with an amount of shielding material that is introduced.
Figure 13:
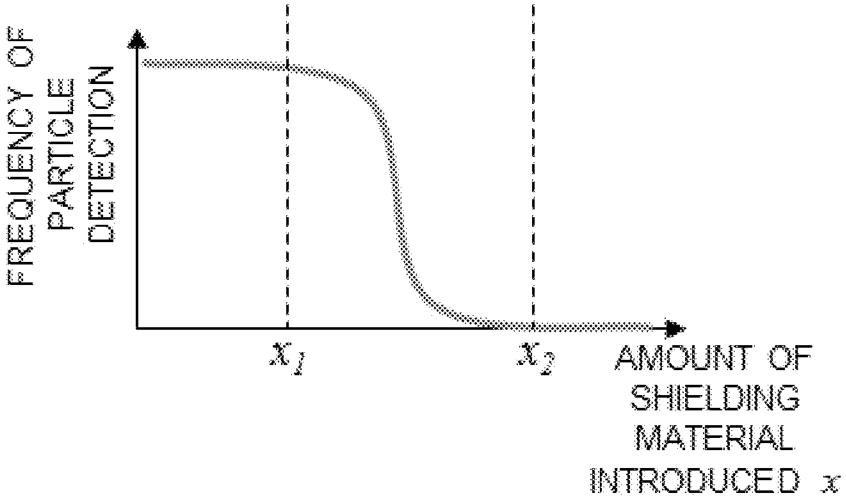
FIG. 13 is a graph illustrating the relationship between the amount of shielding material that has been introduced and the frequency at which particles are detected.

Also, as a method that does not involve the use of colored particles, it is possible to observe the lateral spatial distribution relative to the direction of travel of the particle beam by preparing shielding material such as a terminal introduced linearly perpendicular (that is, in an obstructing direction) to the direction of travel of the particle beam (FIG. 12), and finding the relationship between the amount of shielding material introduced and the amount of particles detected. For example, taking x to be the amount of introduced shield material 41 illustrated in FIG. 12, when the particles have been introduced at a fixed concentration, the frequency at which scattered light is detected should be fixed under steady-state conditions provided that there is no shielding. When the introduced amount x is increased in this state, as illustrated in FIG. 13, in a case where, when the detection region decreases from a certain point $x_1$ and light scattering ceases to be detected at $x_2$, if the spatial distribution of the concentration of particles in the particle beam is a Gaussian-shaped distribution with the center of the particle beam at the apex, the relationship between the amount of shielding material introduced and the frequency of particle detection constitutes an aberration relationship, and the difference therebetween $x_2-x_1$ becomes the particle beam distribution range. Using a method like this also, when the corresponding relationship between the particle beam spatial spread determined using this method and, for example, the frequency distribution of the scattered light intensity (or pulse width) using the method in the present invention has been acquired in advance, it is possible to measure the spatial distribution in a detection region with respect to a frequency distribution obtained for a specific particle beam to be inspected.

[Method for Confirming that the Width of Light Directed at the Particles is Large Enough for the Particle Beam]

In the present invention, it is desirable that the width of the light directed on the particle beam be sufficiently large with respect to the particle beam distribution range to enable all of the observation-slated particles comprising the particle beam to be observed. The following method can be given as a method for confirming this.

Figure 14:
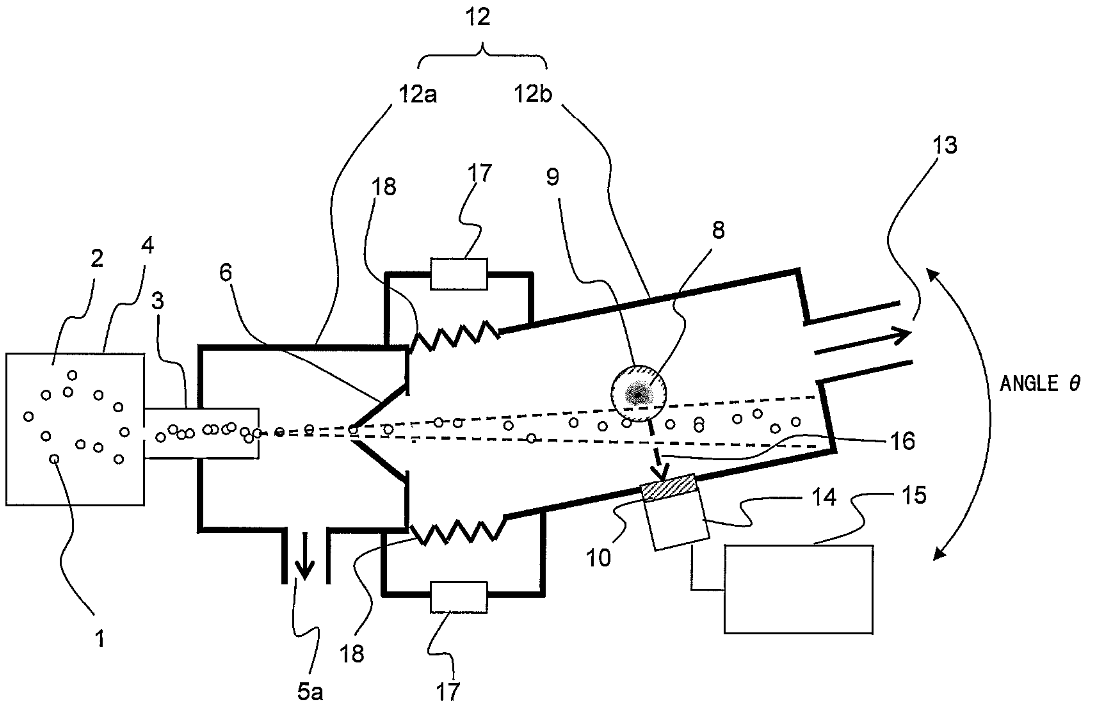
FIG. 14 is a side view of a configurational overview showing an example of the particle beam forming device pertaining to the fourth embodiment of the present invention when in use.
Figure 15:
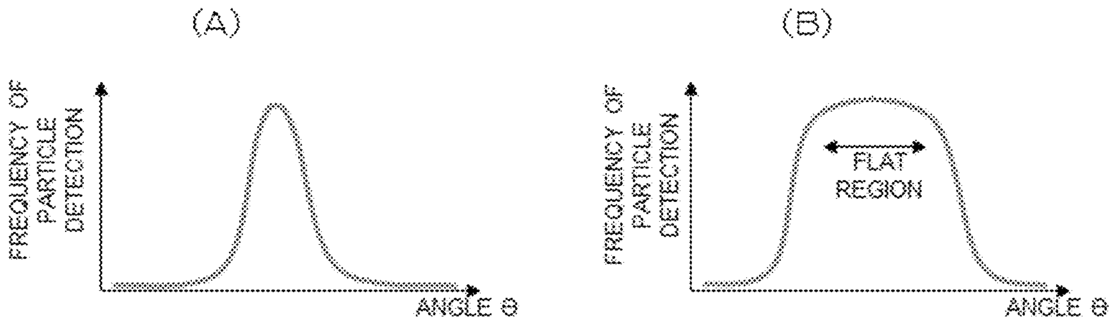
FIG. 15 shows graphs of the relationship between the angle θ of the particle beam and the frequency of particle detection, FIG. 15A being an example of when the distribution range of the particle beam is exactly the same or less than the width of a directed light.
Figure 16:
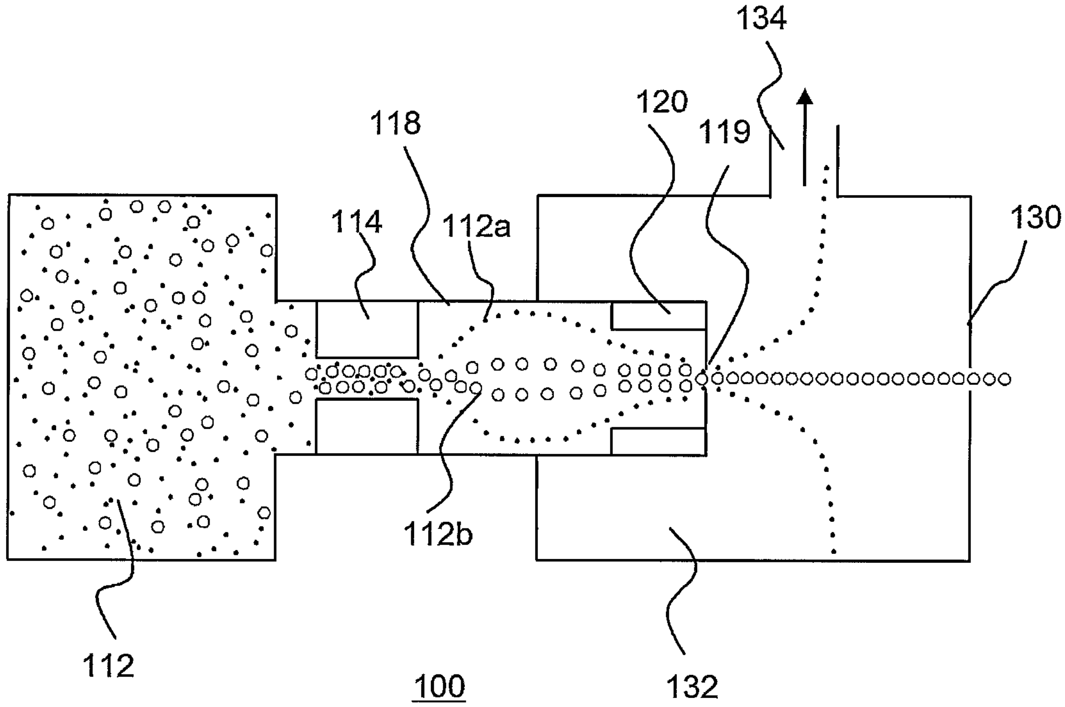
FIG. 16 is a configurational diagram of particle beam forming means comprising one part of a conventional particle beam forming device.

That is, for example, using the particle beam forming device pertaining to the above-described fourth embodiment, the angle of the downstream exhaust chamber is intentionally changed relative to the upstream exhaust chamber as illustrated in FIG. 14. In a case where the width of the directed light is exactly the same or less (the directed light is narrower) than the particle beam distribution range, a graph of a Gaussian-shaped distribution without a flat region is obtained when the angle in FIG. 14 is represented on the horizontal axis and the frequency of particle detection is represented on the vertical axis as illustrated in FIG. 15A. Alternatively, a graph like that of FIG. 15B is obtained when the width of the directed light is broadened sufficiently. In so doing, it is possible to confirm that the directed light is large enough for the particle beam distribution range.

DESCRIPTION OF NUMERALS AND CHARACTERS

1 Particle
2 Particle source
3 Particle beam generating means
4 Storage container
5*a*, 5*b* Exhaust ports
6 Skimmer
7*a* Particle flow lateral spread (upper limit)
7*b* Particle flow lateral spread (lower limit)
8 Laser light
9 Light-transmitting window
10 Light collection optical system (lens)
11 Laser light generating means
12 Reduced-pressure vessel
12*a* Upstream exhaust chamber
12*b* Downstream exhaust chamber
13 Exhaust port serving as particle beam output port
14 Light-scattering detection means
15 Signal processing means (CPU)
16 Scattered light
17 Extension/contraction device (actuator)
18 Operation mechanism (bellows)
19 Extension/contraction device driver
20 Angle adjusting means for particle beam generating means
21*a* Particle passing through center of laser light having Gaussian intensity distribution
21*b* Particle that deviates from center of laser light having Gaussian intensity distribution

22*a* Change over time in scattered light intensity of 21*a*
22*b* Change over time in scattered light intensity of 21*b*

The invention claimed is:

1. A particle beam forming device for forming either a linear or conical particle beam from a particle source in which particles are dispersed in a gas, the particle beam forming device comprising:

a reduced-pressure vessel in which a pressure is reduced;

a particle beam generating unit, which has a first end arranged outside of the reduced-pressure vessel and a second end arranged inside the reduced-pressure vessel, and which captures the particle source from outside the reduced-pressure vessel and introduces the particle beam into the reduced-pressure vessel; and a particle beam evaluating unit for evaluating a spatial distribution of the particle beam inside the reduced-pressure vessel, wherein the particle beam evaluating unit comprises:

a light directing unit for directing light on the particle beam;

a light-scattering detection unit for detecting scattered light generated when the light that has been directed on the particle beam hits the particles; and a signal processing unit for recording and processing a signal outputted from the light-scattering detection unit in accordance with at least one of an intensity and a frequency of detection of the scattered light, wherein the signal processing unit calculates a spatial spread of the particle beam based on at least one of an intensity-spanning frequency distribution and a pulse width-spanning frequency distribution of the scattered light, and based on a relationship between a predetermined spatial intensity distribution of the light and the spatial spread of the particle beam, and wherein the signal processing unit calculates the spatial spread of the particle beam at a plurality of locations following a direction of travel of the particle beam based on signals from the plurality of locations, and calculates a spread angle of the particle beam from the spatial spread at each location.

2. The particle beam forming device according to claim 1, further comprising an adjusting unit for adjusting the spatial distribution of the particle beam based on at least one of the spatial spread and the spread angle of the particle beam determined by the signal processing unit.

3. The particle beam forming device according to claim 2, wherein the adjusting unit for adjusting the spatial distribution of the particle beam includes at least one unit selected from the group consisting of:

a unit for adjusting a length in a path that the particle beam travels of the downstream exhaust chamber of the reduced-pressure vessel;

a unit for adjusting an angle of the downstream exhaust chamber relative to the upstream exhaust chamber; and a unit for adjusting the angle of the particle beam generating unit relative to the upstream exhaust chamber.

4. The particle beam forming device according to claim 1, wherein the particle beam generating unit comprises a device for emitting particles through the particle source in either a linear or conical shape inside a tubular structure provided with a focusing mechanism provided upright on an inner side of the tubular structure.

5. The particle beam forming device according to claim 1, wherein:

the reduced-pressure vessel is divided into an upstream exhaust chamber in which the particle beam generating unit is arranged and a downstream exhaust chamber in which the particle beam evaluating unit is arranged, a skimmer, which comprises a substantially conical through-hole through which the particle beam passes, is disposed in a partition separating the upstream and downstream exhaust chambers, wherein a narrow opening of the skimmer is disposed on a side of the upstream exhaust chamber, and the downstream exhaust chamber is at a lower pressure than the upstream exhaust chamber so as to enable exhausting to be performed respectively therefrom.

6. The particle beam forming device according to claim 5, wherein the downstream exhaust chamber is provided with an output port for extracting the particle beam from the downstream exhaust chamber.

7. The particle beam forming device according to claim 1, wherein the light directing unit comprises a laser light generating unit, and a light-transmitting window which is disposed in the reduced-pressure vessel, and is adapted to transmit the laser light directed by the laser light generating unit.

8. The particle beam forming device according to claim 1, wherein the light directing unit and the light-scattering detection unit are disposed in a plurality of locations at a prescribed spacing in the reduced-pressure vessel following a direction of travel of the particle beam.

* * * * *